United States Patent [19]

Kotzsch et al.

[11] 4,048,374

[45] Sept. 13, 1977

[54] FUNCTIONAL ORGANOPHOSPHONIC ACID ESTERS AS PRESERVATIVE ADHESION PROMOTING AGENTS AND COATING FOR METALS

[75] Inventors: Hans-Joachim Kötzsch; Claus-Dietrich Seiler, both of Rheinfelden; Hans-Joachim Vahlensick, Wehr, Baden, all of Germany

[73] Assignee: Dynamit Nobel Aktiengesellschaft, Troisdorf, Germany

[21] Appl. No.: 590,642

[22] Filed: June 26, 1975

Related U.S. Application Data

[62] Division of Ser. No. 502,125, Aug. 30, 1974.

[30] Foreign Application Priority Data

Sept. 1, 1973  Germany .............................. 2344197

[51] Int. Cl.$^2$ .......................... B05D 1/36; B05D 3/02; B05D 7/14; B05D 7/16
[52] U.S. Cl. ...................................... 428/457; 427/384; 427/386; 427/388 D; 427/409; 427/410; 427/413; 427/417
[58] Field of Search ................... 427/388 R, 409, 410, 427/384, 386, 388 D, 413, 417; 106/14; 428/457; 148/6.5 R

[56] References Cited

U.S. PATENT DOCUMENTS

| | | | |
|---|---|---|---|
| 2,627,521 | 2/1953 | Coover | 260/348 R |
| 2,636,257 | 4/1953 | Ford | 427/409 X |
| 2,770,610 | 11/1956 | Hardy et al. | 260/45.8 |
| 3,154,438 | 10/1964 | Keller et al. | 427/409 X |
| 3,196,039 | 7/1965 | Herbst et al. | 427/388 R X |
| 3,202,534 | 8/1965 | Duch et al. | 427/388 R |
| 3,241,983 | 3/1966 | Bretz | 106/14 |
| 3,380,837 | 4/1968 | Wagner et al. | 106/14 |
| 3,625,716 | 12/1971 | King et al. | 106/14 |
| 3,630,790 | 12/1971 | Schmidt et al. | 106/14 X |
| 3,925,245 | 12/1975 | Harris et al. | 106/14 X |

Primary Examiner—James R. Hoffman
Attorney, Agent, or Firm—Burgess, Dinklage & Sprung

[57] ABSTRACT

A method for protecting the surface of a metal surface which comprises applying to said surface an organophosphorus compound of the formula

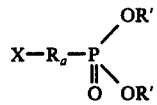

wherein
a is 0 or 1
R is a branched or unbranched chained bivalent alkylene radical of 1 to 12 carbon atoms which is substituted or unsubstituted and can contain in the chain structure —O—, —S—,

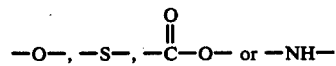

R' is a branched or unbranched alkyl radical of 1 to 12 carbon atoms which can be halogen substituted and can contain in the chain structure

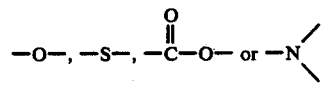

X is an epoxy ring, halogen, alkylene, carboxylic acid ester residue, amino, isocyanato, isothiocyanato, urea, thiourea, urethano, alkyl substituted thio radical or the radical or a heterocyclic ring containing O, S, or N in the ring structure; a new organophosphorus compounds having the formula set forth above and more particularly defined by specific chemical structures.

26 Claims, No Drawings

FUNCTIONAL ORGANOPHOSPHONIC ACID ESTERS AS PRESERVATIVE ADHESION PROMOTING AGENTS AND COATING FOR METALS

This is a division of application Ser. No. 502,125, filed Aug. 30, 1974.

BACKGROUND OF THE INVENTION

1. Field of the Invention

This invention relates to the use of organophosphorus compounds as a protective or preservative coating for metallic surfaces. This invention also relates to the use of certain organophosphorus compounds for promoting adhesion between an organic substance and a metallic surface. This invention is also directed to certain new organophosphorus compounds.

2. Discussion of the Prior Art

Organophosphorus compounds generally are well known and organophosphonic acid esters have been known heretofore. These materials have a wide variety of end uses. Some of them have been used for the modification, e.g. cross-linking or plasticizing of plastics while others have been employed to impart an insecticidal function to a composition. Halogenated organophosphonic acid esters have been used as flame proofing agents. Glycidyl phosphonic acid diethyl ester itself has been found to be useful as an antibiotic.

It has become desirable to find other fields of utility for organophosphonic acid esters. It has also been desirable to provide a means by which metallic surfaces can be protected against the corrosive effects of the atmosphere, especially salt water. It has also become desirable to provide a means by which certain organic substances, e.g. plastics, resins, rubber paints, lacquers and varnishes can adhere to such metallic surfaces. Moreover, it has become desirable to provide a corrosion inhibiting agent which will adhere firmly to a metallic surface such that when it is thereafter applied thereto an organic substance such as a paint lacquer resin or plastic corrosion from within is minimized whereby the coated object has a prolonged life with respect of corrosion.

SUMMARY OF THE INVENTION

In accordance with the present invention it has been found that organophosphonic acid esters are excellent corrosion inhibiting agents for metallic surfaces. It has also been found that these materials provide an exceptionally good adhesion of an organic substance, as more particularly defined hereinafter, to a metallic surface. Thus it has been found that organophosphonic acid esters having the following formula

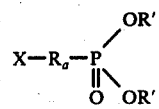

wherein a is 0 or 1

R is a branched or unbranched chained bivalent alkylene radical of 1 to 12 carbon atoms which is substituted or unsubstituted and can contain in the chain structure

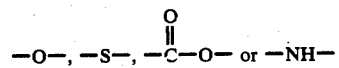

R' is a branched or unbranched alkyl radical of 1 to 12 carbon atoms which can be halogen substituted and can contain in the chain structure

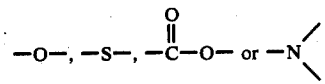

X is an epoxy ring, halogen, alkylene, carboxylic acid ester residue, amino, alkyl substituted thio radical or the radical or a heterocyclic ring containing O, S or N in the ring structure, are especially useful in providing a corrosion-proofing function to metallic surfaces.

The term "corrosion-proofing agents", as used hereinafter, is intended to cover the use of these compounds as a preservative or protective coating as well as their use as an agent for the promotion of adhesion between a metallic surface and a subsequent surface applied thereto such as another protective layer of synthetic or natural polymeric material a for example paints, lacquers, varnishes, rubbers, plastics and resins.

Thus the present invention contemplates a method for protecting a metallic surface in which an organophosphonic acid ester of the above formula is applied to the surface. The same can be applied in a partially or completely saponified form. The term "partially or completely saponified" refers to compounds which can contain free phosphonic acid groupings formed by hydrolysis. In such case R' hydrogen.

Generally speaking the organophosphonic acid esters are applied to the surface of a metal in an amount between 0.5 and 200, preferably between 1 and 80 grams per square meter. The same can be applied in the form of a solvent such as an alcoholic solvent. Other solvents which can be used include: Water, ketones, esters, ethers, e.g. acetone, butanone, methanol, ethanol, ethylene glycol, glycerine, pentaerythnite, diethylene glycol, diethylene glycol, diethylene glycol diacetote, diethylene glycol dimethylether and mixtures thereof. The manner by which the surface is treated is not particularly critical inasmuch as the application of the organophosphonic acid ester to the metal surface can be effected by immersion, spraying or brushing. This treatment is generally followed by heat treatment of the so treated surface. This so-called "heat treatment" is performed by allowing the material to be maintained for a period of time say between 2 and 45 minutes at a temperature between room temperature and up to 300° C, with time and temperature being inversely proportional to one another. The purpose of subjecting the so-treated surface to such temperatures is to harden the surface. Elevated temperatures are employed also to remove any solvent which may be employed. It should be realized, however, that even higher temperatures, above 300° C, can be used if shorter periods of time are employed. Surprisingly metal surfaces thus treated, even when exposed for long periods of time in a corrosive atmosphere show no corrosion. This finding enables the use of these compositions to be employed as a shop primer.

When compounds are used as a preservative or protective coating the procedure is generally to treat the surface of the metal in question with the organophosphonic acid ester which can be partially or completely saponified. To the extent that the esters are fluid at room temperature and may be applied directly to the surface to be protected or they may be first dissolved in a suitable solvent. When they are used as a "shop primer" a solvent is generally employed.

It is also been found that in addition to their use as a shop primer organophosphonic acid esters are suitable as a protective coating for a metal. In this case the metal surface is coated with a hardened or unhardened film of organophosphonic acid ester which again can be partially or completely saponified. Essentially, the process by which the metal is treated is the same as in the case of a shop primer but the treatment is preferably performed repeatedly, each treatment being followed by a hardening at an elevated temperature, especially at a temperature greater than 100° C.

It has also been discovered, in accordance with this invention, that these phosphonic acid esters whether unsaponified, partially saponified or completely saponified, additionally function to improve the adhesion of organic substances to metallic surfaces. The adhesion improving function can be accomplished in two different manners. A metallic surface can be treated with an organophosphonic acid ester, say while dissolved in a solvent, and any solvent can be evaporated thereto. In such case the surface of the metal is treated with between 0.5 and 40 grams per square meter of organophosphonic acid ester. Thereafter there is supplied to the so-treated surface the organic substance. The organic substance can be a conventional protective coating of a synthetic or natural organic material, such as a paint, lacquer, resin, plastic or rubber. The adhesion of such materials is vastly improved.

On the other hand, the adhesion of the organic substance can be improved by directly incorporating the organophosphonic acid ester into the organic substance in which case pretreatment of the metallic surface need not be performed. In such case there is also provided the anti-corrosive protective of the metal owing to the presence of the organophosphonic acid ester in the coating on the metal. Also the organic substance adheres to a greater extent to the metal surface than is obtained without the use of organophosphonic acid ester. Whether the surface is pretreated with organophosphonic acid ester or the same is incorporated in the organic composition makes little difference as in both instances the anti-corrosive protection of the metal is obtained to the full extent which corrosion protection is of a long lasting nature.

DESCRIPTION OF SPECIFIC EMBODIMENTS

The invention has been described above in one of its broader aspects as the use of organophosphorous compounds of the specified formula. Referring to that formula X is an epoxy ring, halogen, alkenyl, carboxylic acid residue, amino, alkyl substituted thio radical or a heterocyclic radical containing oxygen sulfur or nitrogen in the ring. When X is halogen it is preferred that it be chlorine or bromine. When X is alkenyl it is preferred that the alkenyl group have been 2 and 8 carbon atoms therein. When X is a carboxylic acid ester residue it is preferred that the ester function itself be made of especially an alkyl group of 1 to 8 carbon atoms. The carboxylic acid side of the carboxylic acid ester residue is generally composed of a chain of between 2 and 8 carbon atoms attached to the carbonyl carbon atom. When X is an alkyl substituted thio radical it is preferred that the alkyl group of that thio radical have been 1 and 8 carbon atoms therein. When X is a heterocyclic ring it is preferred that the heterocyclic ring contain between 3 and 7 members in the ring.

Referring once again to the formula the value R is stated to be a branched or unbranched chained bivalent alkylene radical of 1 to 12 carbon atoms. Preferably R is a bivalent alkylene radical of between 1 and 8 carbon atoms. The same can be substituted or unsubstituted. When substituted it can be substituted by any one of the following groups: Epoxy ring halogen, alkylene, carboxylic acid ester residue, amino, isocyanato, isothiocyanato, urea, thiourea, urethano, alkyl substituted thio radical or the radical or a helerocyclic ring containing O, S or N in the ring structure.

The R group can also contain a bivalent radical of the formula

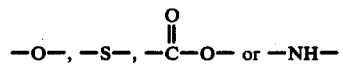

in the chain of the structure.

The value R' is stated to be a branched or unbranched chain alkyl radical of 1 to 12 carbon atoms. Preferably R' is a branched or unbranched alkyl radical having between 1 and 8 carbon atoms in the chain. Of course when the organophosphonic acid ester has undergone partial or complete saponification the value R' will be hydrogen. When R' is an alkyl radical it can be substituted by a halogen group, e.g., chlorine, bromine or it can have within this chain structure a bi- or tri-valent radical of the formula

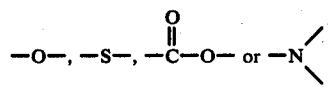

This intensive adhesion promotion is based partially on a genuine chemical binding of the substance used as the adhesion promoting agent pursuant to the invention, and partially on paravalent or adhesive binding according to how the organofunctional radical of the adhesion promoting agent is adapted to the chemistry of the organic substance of which the coating consists. In some cases, the claimed organophosphonic acid esters are to be combined in their use pursuant to the invention with adjuvants such as, for example, solvents, plasticizers, fillers, hardeners, dyes, etc. These adjuvants can be present in an amount of between 1 and 99 percent by weight, based on the weight of the organophosphonic acid ester.

The unexpected high practical effect resulting from this is beneficial in a great number of technical applications, since metal corrosion is a primary factor in the economy. For example, in the methods commonly used today for coating metals with plastics, e.g., the fluid bed process or the various methods used in preparing laminates from metals and applied plastic films or foam plastic layers, separation frequently occurs due to the lack of sufficient adhesion between the two confronting surfaces, resulting not only in a loss of the physical characteristics of the laminate, but also in the disadvantage of special sensitivity to corrosion on the metal side.

This disadvantage is especially evident in the case of lacquer and paint finishes, whose tendency to rust from underneath, for example, which is notorious even among non-technical people, requires considerable expense in maintenance and repair.

On the other hand, the improvement of the strength of adhesion in the boundary surface between metal and organic material is of very special importance in systems subject to great mechanical stress. A field in which the use of the claimed organophosphorus compounds in accordance with the - invention therefore represents a considerable technical advance is the manufacture of steel belted tires, whose quality can in this manner be improved to a considerable extent, the exclusion of any corrosion of the steel belt offering the additional benefit of a safety improvement.

The finish coatings whose adhesion to metals is improved in accordance with the invention may consist of a great variety of materials. Examples of such materials are the following, which may also be used in modified form, the adhesion-promoting action not being limited thereto: reaction resins of the epoxy, polyester or phenolic type, urea resins, vulcanizable polybutadiene resins, copolymerized if desired with acrylic or vinyl compounds, such as styrene or vinyl acetate for example; also, natural or synthetic latices of olefinically unsaturated forepolymers, or drying oils based on unsaturated fatty acids.

The organophosphonic acid esters are used in accordance with the nature of the finish coat that is to be applied. Organophosphonic acid esters containing epoxy groups have, for example, a special adhesion promoting action with epoxy resins, thermosetting resins and drying oils; compounds of the invention containing halogen or OH and NH$_2$ groups, however, may also be used as adhesion promoting agents with epoxy resins, phenolic resins and urea resins, or with drying oils. When included in the resins the organophosphonic acid ester is present in an amount between 1 and 99% by weight based on the weight of the resin.

Organophosphonic acid esters containing double bonds are used preferentially as adhesion promoting agents with natural or synthetic types of rubber, such as the vulcanizable polybutadienes or their copolymers with acrylic and/or vinyl compounds. The vulcanization in that case may be performed either with peroxides or thermally by means of conventional vulcanization accelerators. For the latter part, organophosphonic acid esters containing sulfur are also very well suited, such as 3-N-phenylthioureido-propanephosphonic acid diethyl ester, for example. Such double bond containing phosphonic acid esters are employed in amounts between 0.1 and 20 percent by weight based on the weight of resin when included in the resin itself.

Organophosphonic acid esters containing double bonds may also be used to advantage as adhesion promoters for polyester resins, particularly those which contain unsaturated, hardenable and cross-linking forepolymers, such as, for example, systems of maleic acid polycondensates and vinyl benzene compounds. Also the adhesion of drying oils to metal surfaces can be substantially improved by means of organophosphonic acid esters, partially or completely saponified if desired, and containing double bonds.

From what has been said above it is apparent that organophosphonic acid esters with a wide variety of functional groups can be used in accordance with the invention. From among the great numbers of usable compounds the following, identified by formula, are named by way of example:

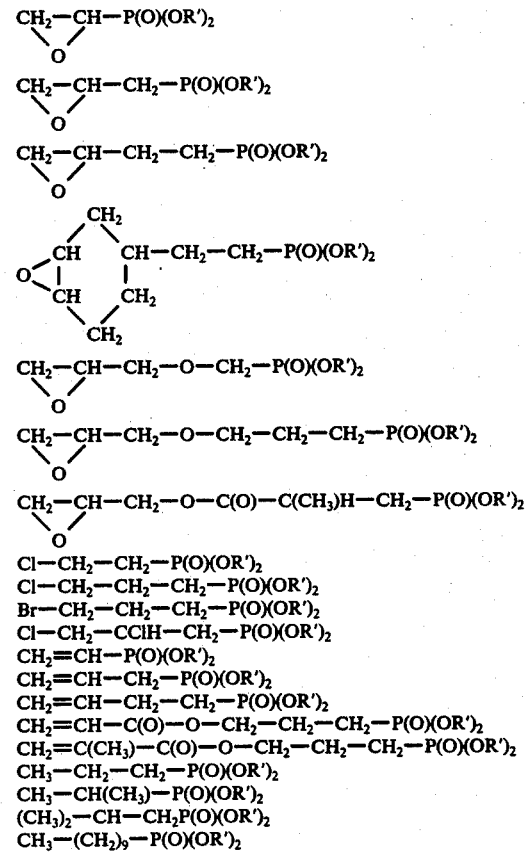

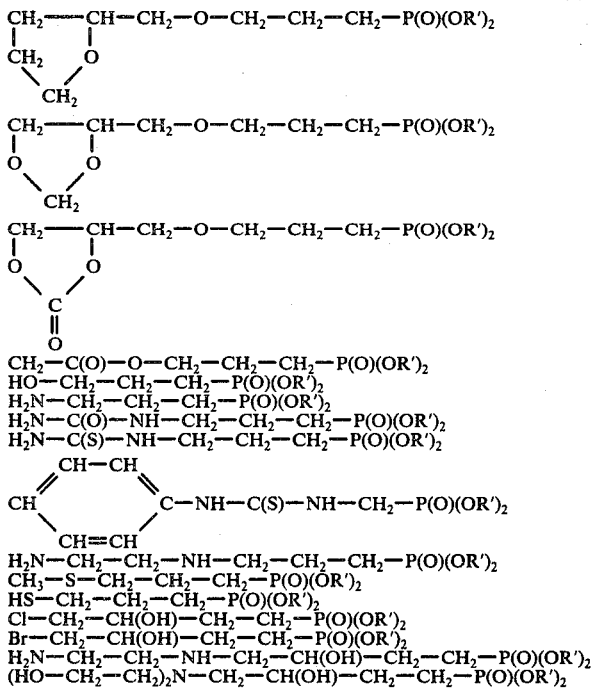

```
CH₂—C(O)—O—CH₂—CH₂—CH₂—P(O)(OR')₂
HO—CH₂—CH₂—CH₂—P(O)(OR')₂
H₂N—CH₂—CH₂—CH₂—P(O)(OR')₂
H₂N—C(O)—NH—CH₂—CH₂—CH₂—P(O)(OR')₂
H₂N—C(S)—NH—CH₂—CH₂—CH₂—P(O)(OR')₂
```

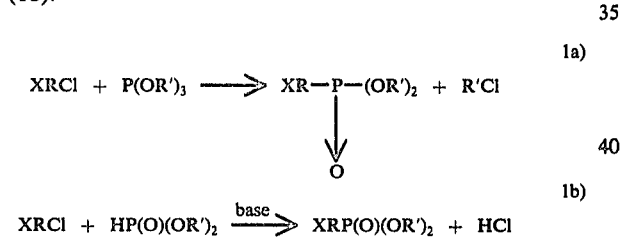

```
H₂N—CH₂—CH₂—NH—CH₂—CH₂—CH₂—P(O)(OR')₂
CH₃—S—CH₂—CH₂—CH₂—P(O)(OR')₂
HS—CH₂—CH₂—CH₂—P(O)(OR')₂
Cl—CH₂—CH(OH)—CH₂—CH₂—P(O)(OR')₂
Br—CH₂—CH(OH)—CH₂—CH₂—P(O)(OR')₂
H₂N—CH₂—CH₂—NH—CH₂—CH(OH)—CH₂—CH₂—P(O)(OR')₂
(HO—CH₂—CH₂)₂N—CH₂—CH(OH)—CH₂—CH₂—P(O)(OR')₂
```

Depending on the nature of the functional radical, the preparation of these compounds is carried out in accordance with a number of variants of the Arbusov Reaction as expressed by the following equation (1a) and (1b):

$$XRCl + P(OR')_3 \longrightarrow XR-P-(OR')_2 + R'Cl \quad (1a)$$
$$\Big\downarrow O$$

$$XRCl + HP(O)(OR')_2 \xrightarrow{base} XRP(O)(OR')_2 + HCl \quad (1b)$$

The symbols XR and R' have the same meaning here and in the following equations as they did in the Formula (1) given at the beginning of this description; X in this case does not mean, of course, any grouping that might interfere with the Arbusov reaction.

By means of the radical addition of suitable, olefinically unsaturated compounds onto dialkyl phosphites in a known manner, compounds of the General Formula (1) are accessible in which the radical X concists of a carboxylic acid ester group, an amino group, a substituted amino group, a hydroxyl group, a thiol group, a substituted thio group or of a heterocyclic group containing O, S and/or N.

Organophosphonic acid esters of the General Formula (1), in which X is a substituted or unsubstituted thio or amino group, can also be prepared by halogen exchange in accordance with reaction equations (2a) and (2).

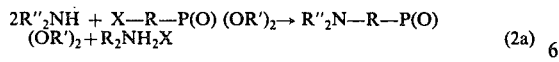

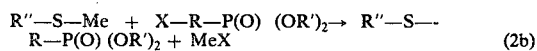

(Me = alkali metal, R" = H or alkyl, aryl or cycloalkyl)

Another method of preparation is, for example, the decyclization reaction of epoxides with acids or acid anhydrides of amines in accordance with reaction equations (3a), (3b) and (3c).

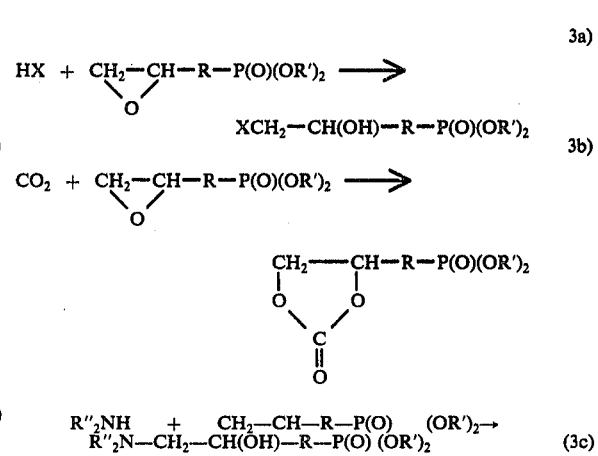

(R" same as in equations (2a) and (2b))

However, a number of other methods currently practices in organic synthesis may be used for the preparation of the substances of the invention.

Suitable metals for the application, in accordance with the invention, of the claimed substances are primarily iron, especially in the form of the various types of steel, such as carbon steels for example, but also alloy steels containing, for example, manganese, nickel, vanadium, chromium, molybdenum, tungsten, etc.

It has also been discovered that several new phosphonic acid esters can be utilized for the same purposes as set forth above, i.e., as corrosion proof agents, protective coatings, adhesion augmenting agents and the like. New phosphonic acid esters are those having the following formulae:

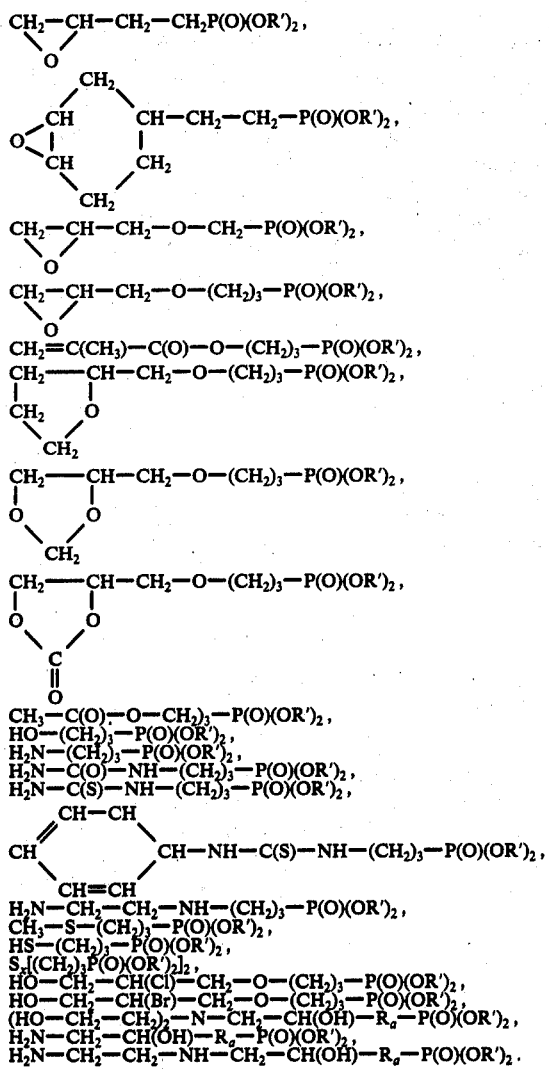

These are novel phosphonic acid esters and can be prepared, at least in some instances, by the reactions set forth above. In the ensuing disclosure there is set forth by which various phosphonic acid esters can be prepared. The following examples also show the manner by which the phosphonic acid esters are used as a protective coating for a metal surface and/or as an adhesion augmenting agent.

EXAMPLE 1

Preparation of 3-glycidyloxypropanephosphonic acid diethyl ester

In a flask having a capacity of 500 ml. equipped with stirrer, thermostatic temperature control, relfux condenser, dropping funnel and internal thermometer, 76 grams of diethylphosphite were heated to 140° C.

Then a water-free mixture consisting of 69 g of diethylphosphite, 114 g of allylglycide ether and 21.6 g of tertiary-butylper-2-ethylhexoate was added drop by drop over a period of 1 hour, with stirring, while the temperature was maintained at 140° C.

After completion of the above addition the mixture was maintained at 140° C for another 40 minutes. The gas chromatographic analysis of the crude product shows a content of approximately 89% 3-glycidyloxy-propanephosphonic acid diethyl ester. Vacuum distillation produces 227 g of pure product.

Boiling point: 131° C (2 Torr)
$D_4^{20}$: 1.106
$n_D^{25}$: 1.4478

| Elemental Analysis Calculated for $C_{10}H_{21}O_5P$ | C | H | P |
|---|---|---|---|
| (molecular weight 252.3) | 47.7% | 8.4% | 12.3% |
| Found | 48.0% | 8.6% | 12.2% |

Epichlorhydrin Derivative

In a flask having a capacity of 500 ml, equipped with stirrer, thermostatic temperature control, bottom valve, reflux condenser, dropping funnel and internal thermometer, 50.5 g of 3-glycidyloxypropanephosphonic acid diethyl ester was dissolved in 200 ml of transdichloroethylene. While maintaining a temperature of 25° C, 30 g of concentrated hydrochloric acid was stirred in over a period of 10 minutes, resulting in a slight self-heating. Stirring is continued for 10 more minutes, the supernatant water is separated, the remainder is washed with 5% sodium bicarbonate and dried with sodium sulfate, and the solvent is removed by distillation, a vacuum being applied in the final stage, and the still temperature being kept below 60° C. 3-(3'-hydroxy-2'-chloropropoxy)propane-phosphonic acid diethyl ester remaining in the residue in the form of a pale yellow, viscous oil.

| Elemental Analysis of Desired Phosphonic Acid Ester Calculated for $C_{10}H_{22}ClO_5P$ | C | H | Cl | P |
|---|---|---|---|---|
| (molecular weight 287.7) | 41.8% | 7.7% | 12.3% | 10.8% |
| Found | 42.2% | 7.8% | 12.7% | 10.6% |

The epibromohydrin derivative was prepared in a perfectly analogous manner using transdibromoethylene.

EXAMPLE 2

Preparation of a glycidylphosphonic acid dimethyl ester

In a flask having a capacity of 500 ml, equipped with a stirrer, thermostatic temperature control, reflux condenser, dropping funnel and internal thermometer, 0.5 g of vanadium (III) acetylacetonate is dissolved in 120 ml of acetone (previously purified with $KMnO_4$). Then 75 g (0.5 mole) of allylphosphonic acid dimethyl ester is mixed in. With intense stirring, 65 ml of 30% hydrogen peroxide is added by drop over a period of about 20 minutes at 30° C. Then the mixture is refluxed for 2 hours, after which the acetone is largely removed by distillation, whereupon the product separates as the heavy phase. The aqueous phase is extracted with methylene chloride. 77 grams of glycidylphosphonic acid dimethyl ester are obtained by vacuum distillation.

Boiling Point: 109° C (4 Torr)
$D_4^{20}$: 1.132
$n_D^{25}$: 1.4421

| Elemental Analysis: Calculated for $C_5H_{11}O_4P$ | C | H | P |
|---|---|---|---|
| (molecular weight 166.1) | 36.1% | 6.6% | 18.7% |
| Found | 36.2% | 6.8% | 18.5% |

EXAMPLE 3

Preparation of 3-(2',4'-dioxacylopentyl)-methoxypropanephosphonic acid diethyl ester The same procedure is followed as in Example 1, but 144 g of 4-allyloxymethyl-1,3-dioxolane of the formula is used instead of the allyl glycide ether. 343 g of pure product is the result.

Boiling Point: 138° C (1 Torr)
$D._4^{20}$: 1.021
$n_D^{25}$: 1.4483

| Elemental Analysis: Calculated for $C_{11}H_{23}O_6P$ | C | H | P |
|---|---|---|---|
| (molecular weight 282) | 46.8% | 8.2% | 11.0% |
| Found | 47.0% | 8.5% | 10.8% |

EXAMPLE 4

Preparation of 3-(3',5'-dioxacylohexyloxy)-propanephosphonic acid diethyl ester

Example 1 is repeated using 144 g of 5-allyloxy-1,3-dioxane, resulting in 236 g of pure product.

Boiling Point: 135° C (1 Torr)
$D._4^{20}$: 1.035
$n_D^{25}$: 1.4481

| Elemental Analysis: Calculated for $C_{11}H_{23}O_6P$ | C | H | P |
|---|---|---|---|
| (molecular weight 282) | 48.8% | 8.2% | 11.0% |
| Found | 46.9% | 8.5% | 11.0% |

EXAMPLE 5

Preparation of decanephosphonic acid diethyl ester

Example 1 is repeated using 140 g of decene-(1) and 5.84 g of ditertiarybutlyperoxide at 150° C. An 84% yield of pure product is obtained.

Boiling Point: 138° C (1 Torr)
$D._4^{20}$: 0.937
$n_D^{20}$: 1.4370

| Elemental Analysis: Calculated for $C_{14}H_{31}O_3P$ | C | H | P |
|---|---|---|---|
| (molecular weight 278) | 60.2% | 11.4% | 10.8% |
| Found | 60.4% | 11.2% | 11.1% |

EXAMPLE 6

Preparation of octanephosphonic acid diethyl ester

Example 5 is repeated using 112 g of octene-(1). An 82% yield of pure product is obtained.

Boiling Point: 115° C (0.5 Torr)
$D._4^{20}$: 0.948
$n_D^{20}$: 1.4330

| Elemental Analysis: Calculated for $C_{12}H_{27}O_3P$ | C | H | P |
|---|---|---|---|
| (molecular weight 250) | 57.6% | 10.8% | 12.4% |
| Found | 57.9% | 11.1% | 12.1% |

EXAMPLE 7

Preparation of isobutanephosphonic acid diethyl ester

In a 10-liter flask with stirrer, internal thermometer, reflux condenser (−80° C) and a cooled dropping funnel, 2070 g of Methylphosphite is heated to 150° C. Then over a period of about 90 minutes a mixture of 2070 g of diethylphosphite, 1680 g of isobutene and 44 g of ditertiarybutyl peroxide is added drop by drop. The reaction heat that develops is removed by external cooling. Then heating at 150° C continues for about 30 minutes. Vacuum distillation through a 12-tray column delivers an 81% yield of pure product.

Boiling Point: 74° C (2 Torr)
$D._4^{20}$: 0.985
$n_D^{20}$: 1.4209

| Elemental Analysis: Calculated for $C_8H_{19}O_3P$ | C | H | P |
|---|---|---|---|
| (molecular weight 194) | 49.5% | 9.8% | 16.0% |
| Found | 49.5% | 9.7% | 15.8% |

EXAMPLE 8

Preparation of 3-(2',4'-dioxa-3'-oxocyclopentyl)-methoxypropane-phosphonic acid diethyl ester In a one-liter autoclave with stirrer, 252 g of 3-glycidyloxypropane-phosphonic acid diethyl ester containing 100 mg. of tetraethylammonium bromide is heated for 3 hours at 110° C. under carbon dioxide at a pressure of 40 atmospheres gauge. Vacuum distillation then yields 283 g. of pure product.

Boiling Point: 144° C (0.8 Torr)
$D._4^{20}$: 1.098
$n_D^{25}$: 1.4489

| Elemental Analysis: Calculated for $C_{11}H_{21}O_7P$ | C | H | P |
|---|---|---|---|
| (molecular weight 296) | 44.6% | 7.1% | 10.5% |
| Found | 44.5% | 7.3% | 10.7% |

EXAMPLE 9

Preparation of 3-aminopropanephosphonic acid diethyl ester

In a flask with a capacity of 2000 ml., equipped with thermostatic temperature control, reflux condenser, dropping funnel and an internal thermometer, 690 g. of diethylphosphite was heated to 140° C. Then, while maintaining 140° C, a mixture consisting of 552 g. of diethylphosphite, 446 g. of anhydrous allyl amine and 75 g of tertiary butyl peroctoate is added drop by drop over a period of 80 minutes, the temperature being kept at about 144° C by controlling the rate of addition. No refluxng occurs. After the addition of the mixture was complete, an internal temperature of 142° to 153° C. was maintained for 1 hour with the heating system.

Distillation through a thin film evaporator yields 221 g. of first runnings and 1561 g of 3-aminopropane-phosphonic acid diethyl ester as a pale yellow, viscous oil, which at room temperature hardens to amorphous ctystals and which is of sufficiently good quality to satisfy the requirements of its technical application. $D._4^{20}$ 1.060;

soluble in water; crystallizes from benzene in deliquescent prisms.

Elemental Analysis:

| Calculated for $C_7H_{18}NO_3P$ | C | H | N | P |
|---|---|---|---|---|
| (molecular weight 195.2) | 43.4% | 9.3% | 7.2% | 15.9% |
| Found | | | | |

N-Acetyl Derivative 97 g. of 3-aminopropanephosphonic acid diethyl ester is dissolved in 400 ml. of dry pyridine and 55 g. of acetic anhydride is added with stirring. The mixture is then boiled for 4 hours with refluxing and freed of the low-boiling components by evaporation in a light vacuum. Gaschromatographically pure N-acetyl-3-aminopropanephosphonic acid diethyl ester is obtained in a 96% yield by shortcut distillation in vacuo. It is a pale yellow, highly viscous oil with a boiling point of 166° to 160° C (0.4 Torr).

Elemental Analysis

| Calculated for $C_9H_{20}NO_4P$ | C | H | N | P |
|---|---|---|---|---|
| (molecular weight 237.3) | 45.9% | 8.5% | 5.9% | 13.1% |
| Found | 46.0% | 8.7% | 6.0% | 13.0% |

This substance was also independently synthesized from N-allylacetamide and diethylphosphite in a manner analogous to the free amine.

N'-Phenylthiourea Derivative 20 g of 3-aminopropanephosphonic acid diethyl ester was mixed with a solution of 14 g of phenylisothiocyanate in 50 ml. of dry benzene, whereupon a slightly exothermic reaction takes place (temperature rise from 22° C starting temperature to 28° C within 6 minutes due to self-heating), and the product precipitates in crystals. After recrystallization from benzenepentane it melts at 86° to 88° C.

Elemental Analysis

| Calculated for $C_{14}H_{23}N_2O_2PS$ | C | H | N | P | S |
|---|---|---|---|---|---|
| (molecular weight 330.4) | 50.8% | 7.0% | 8.5% | 9.4% | 9.7% |
| Found | 51.2% | 7.2% | 8.8% | 9.2% | 9.8% |

EXAMPLE 10

Preparation of 3-hydroxypropanephosphonic acid diethyl ester

Analogously to Example 9, 2070 g of diethylphosphite was placed in a 4-liter flask and heated to 132° C. A mixture consisting of 690 g of diethylphosphite, 580 g of anhydrous allyl alcohol and 100 g of tertiarybutyl octoate is added drop by drop over a period of 130 minutes while the temperature is kept between 132° and 136° C. Heating is then continued for 30 minutes at 130° C.

Distillation through a thin film evaporator yields, after separation of the excess diethylphosphite, a viscous, colorless oil from which 971 g (76% yield) of 3-hydroxypropanephosphonic acid diethyl ester is separated by shortcut distillation as a highly viscous, water-soluble oil.

Boiling Point: 138° C (0.2 Torr)
$D_4^{20}$: 1.108

Elemental Analysis

| Calculated for $C_7H_{17}O_4P$ | C | H | P |
|---|---|---|---|
| (molecular weight 196.2) | 42.8% | 8.7% | 15.8% |
| Found | 43.0% | 8.8% | 16.0% |

The short-cut distillation leaves a pale yellow, polymeric residue (soluble in a phenol-tetrachloroethane mixture) which is a viscous fluid when heated and is toughly elastic at room temperature.

O-Acetyl derivative 98 g of 3-hydroxypropanephosphonic acid diethyl ester is acetylated analogously to Example 9. 3-acetoxypropanephosphonic acid diethyl ester is isolated in a yield of approximately 100%.

Boiling Point: 102° C (1 Torr)
$D_4^{20}$: 1.104
$n_D^{25}$: 1.4333
Viscosity: 6.91 cSt (25° C)

Elemental Analysis

| Calculated for $C_9H_{19}O_5P$ | C | H | P |
|---|---|---|---|
| (molecular weight 238.2) | 45.4% | 8.0% | 13.0% |
| Found | 45.3% | 8.4% | 13.2% |

The acetate was also synthesized independently from allyl acetate and diethyl phosphite similarly to the free hydroxy compound.

O-Methacrylic Derivative 98 grams of 3-hydroxypropane-phosphonic acid diethyl ester was dissolved together with 2 g of hydroquinone in 400 ml. of dry pyridine. A solution of 52.3 g of freshly distilled methacrylic acid chloride and 1 g of hydroquinone in 100 ml. of dry pyridine is added drop by drop over a period of 10 minutes, with stirring, under nitrogen gas, while maintaining the temperature below 40° C by cooling. Stirring then continues for 20 minutes at 50° C, and then, by the addition of 800 ml. of trans-dichloroethylene, the precipitation of pyridine hydrochloride is completed and the solution is suction filtered. It is concentrated by evaporation at less than 50° C, with the application of a vacuum at the end, and then the product is distilled in a vacuum type rotatory evaporator. The pure yield is 83%.

Boiling Point: 88° C (0.1 Torr)
$D_4^{20}$: 1.062

| Calculated for $C_{11}H_{21}O_5P$ | C | H | P |
|---|---|---|---|
| (molecular weight 264.28) | 49.9% | 8.0% | 11.7% |
| Found | 50.3% | 8.2% | 11.8% |

Phenylurethane Derivative 20 g of 3-hydroxypropane-phosphonic acid diethyl ester is mixed with a solution of 12 g phenylisocyanate in 20 ml. of dry benzene, whereupon the product precipitates in crystals. After recrystallization from benzene-pentane, it melts at 117° to 119° C.

Elemental Analysis

| Calculated for $C_{14}H_{22}NO_5P$ | C | H | N | P |
|---|---|---|---|---|
| (molecular weight 315.3) | 53.3% | 7.0% | 4.5% | 9.9% |
| Found | 53.6% | 7.0% | 4.2% | 9.5% |

EXAMPLE 11

Polycondensation of 3-hydroxypropane-phosphonic acid diethyl ester and its use as a shop primer.

A solution of 5 g of 90% ethanol in 95 g of 3-hydroxypropane phosphonic acid diethyl ester is cast on a steel plate with a slightly rusty surface to form a film which is heat treated at 220° C for 2 hours in a vacuum drying chamber. A tough, scratch-resistant film forms which cannot be separated or dissolved from the metal either mechanically or by boiling in water or pyridine.

EXAMPLE 12

Preparation of 3-methylthiopropane-phosphonic acid diethyl ester

Analogous to Example 1. 88 g of allylmethylsulfide is used instead of the allyl glycide ether. 177 g of pure 3-methylthiopropanephosphonic acid diethyl ester product is the result.

Boiling Point: 88° C (5 Torr).

EXAMPLE 13

Preparation of bis-(3-diethoxyphosphonylpropyl)-disulfide

Analogous to Example 1, except with the drop-by-drop addition of a mixture of 138 g of diethylphosphite, 73 g of diallyldisulfide and 21.6 g of tertiarybutylper-2-ethylhexoate. Crude product refined by vacuum concentration yields, in the distillation residue, 206 g of bis-(3-diethoxyphosphonylpropyl)disulfide as a yellow, viscous oil.

EXAMPLE 14

The use of 3-glycidyloxypropanephosphonic acid diethyl ester as shop primer 60 thin sheets of common structural steel in accordance with DIN Standard 1623 (St. 37) measuring 100 × 40 mm and 0.7 mm thick were degreased with absolute ethanol and then annealed at 500° C. Then they were cooled to 220° C and 30 test specimens were sprayed on both sides by means of a spray gun with a 50% solution of 3-glycidyloxypropanephosphonic acid diethyl ester in 90% ethanol which had previously been refluxed for 1 hour. The coating amounted to about 4 g of active substance per square meter. The remaining 30 test sheets were only sprayed with absolute ethanol, for purposes of comparison. All the sheets were then held at 220° C for another 25 minutes and then cooled. Ten of the test sheets and ten of the controls were protected by welding them in polyethylene film. Ten more of each were exposed to weather on a weathering frame and 10 were placed in a 3% sodium chloride solution.

EXAMPLE 15

The use of isobutanephosphonic acid diethyl ester as a shop primer.

As in Example 14, an 80% preheated solution of isobutanephosphonic acid diethyl ester was sprayed on at 300° C, and then the temperature was maintained at 220° C for 10 minutes. Exposure and judgment were carried out as in Example 14.

Evaluation Table for Examples 14 and 15
Comparison of treated and untreated specimens with one another and with protected specimens.

| | Treated Specimens | | | Untreated Specimens | | |
|---|---|---|---|---|---|---|
| Time | Exposed to weather | Immersed in saline solution | Protected | Exposed to weather | Immersed in saline solution | Protected |
| 4 Days | Bright | Bright | Bright | Slight, uniform rusting | Small spots of rust | Bright |
| 30 Days | Bright | Bright | Bright | Rust coated (solid) | Coarse rust coating | Bright |
| 50 Days | Rust-free (surface dull) | Bright | Bright | Coarse rust coating | Flaking rust coating | Bright |
| 93 Days | Rust-free (surface dull) | Bright | Bright | Flaking rust coating | Flaking rust coating | Bright |

The same observations were made for the treating compositions of Example 15 as made for samples treated with the compositions of Example 14. Hence, the comparative table is applicable with the same effect to the tests and comparisons of both examples.

EXAMPLE 16

Use of 3-glycidyloxypropanephosphonic acid diethyl ester as an adhesion promoting agent for lacquers 120 thin sheets of ordinary structural steel in accordance with DIN Standard 1623 (St. 37) measuring 100 × 40 mm and 0.7 mm thick were degreased with absolute ethanol, dried at 80° C and in groups of 30 each were primed in the manner described below in three spray coats followed by two hours of drying at 130°°C:

Series A

Primed with a preheated 10% solution of 3-glycidyloxypropanephosphonic acid diethyl ester in 70% ethanol.

Series B

Primed with a preheated 10% solution of 3-glycidyloxypropanephosphonic acid diethyl ester in 70% ethanol, previously adjusted with phosphoric acid to pH 4.

Series C

Primed with a common commercial priming lacquer.

Series D

Not primed. Serves as a control.

All of the test sheets of series A to D were then lacquered four times with a commercial light gray automobile lacquer on a polyester basis by spraying and baking at 80° C.

Two sheets of each series were preserved as controls by heat sealing in polyethylene film. At the bottom edge of another seven test sheets from each series, the lacquer was ground away down to the bright metal. The remaining seven test sheets of each series had their lacquer finishes intact.

The four series of test sheets with the cut lacquer edges as well as those with the intact lacquer finish were exposed to the atmosphere on a weathering frame in the one case and submerged in a 3% sodium chloride solution in the other.

On the test sheets with the cut lacquer edges an area of rusting under the finish formed in the course of time, beginning between the lacquer layer and the metal surface at the cut edge. The extent of the rusting could be seen in the rusty discoloration of the lacquer film covering it. Its advance in the course of time is a measure of the quality of the prime coat which is intended to promote adhesion and have an anticorrosive action. Consequently, in the Evaluation Table for Example 16, the width of the rusty area extending from the cut edge is measured in millimeters in relation to time.

Evaluation Table for Example 16

Comparison of the corrosion of the test sheets having the cut lacquer edges with one another and with the samples in which the lacquer remained intact, based on an evaluation of the progress of the corrosion.

| | Width of corrosion zone in mm** on test sheets with cut lacquer edges | | | | | | | | |
|---|---|---|---|---|---|---|---|---|---|
| | Exposed to weather | | | | Submerged in sodium chloride solution | | | | |
| Time | A | B | C | D | A | B | C | D | Controls* |
| 4 days | — | — | — | 4 | 1 | 1 | 1 | 6 | |
| 30 days | 1 | 1 | 1 | 5 | 1 | 2 | 2 | 11 | No obser- |
| 50 days | 1 | 1 | 2 | 9 | 1 | 2 | 4 | 14 | vable |
| 93 days | 1 | 2 | 5 | 12 | 1 | 3 | 7 | 18 | corro- |
| 120 days | 2 | 4 | 7 | 22*** | 2 | 6 | 11 | 34*** | sion*** |

*Test sheets with intact lacquer coating of Series A to D after exposure to weather or submersion in sodium chloride solution.
**Average of seven specimens each
***All specimens of Series D generally have rusty spots in the lacquer after 120 days.

EXAMPLE 17

The use of 3-glycidyloxypropanephosphonic acid diethyl ester as a protective coating 30 sheets of common structural steel in accordance with DIN Standard 1623 (St. 37), measuring 100 × 40 mm and 0.7 mm thick, were degreased with absolute, benzene-denatured ethanol, derusted with phosphoric acid, cleaned again with ethanol, and dried at 80° C. Then the sheets were submerged each for 5 minutes in a mixture consisting of 3-glycidyloxypropanephosphonic acid diethyl ester and 2% triethanolamine (moisture content in the triethanolamine 8%) and hardened for 3 hours at 120° C. This treatment was performed a total of four times on each sheet.

This treatment gave the sheets a glossy, scratch-resistant plastic coating which was very dense and firmly adherent.

On 15 test sheets this plastic coating was ground off at the bottom edge to the bright metal. The coating was left intact on the rest of the sheets.

Five test sheets with the intact plastic coating and five with the plastic coating cut were protected by heat sealing in polyethylene film, five of each type were submerged in 3% sodium chloride solution, and 5 of each type were exposed to the weather. Evaluation was made as in Example 16 by measuring the width of any corroded area that might form.

On the test sheets having the intact plastic coating no traces of corrosion were observed in any case after 120 days. Those having the definitely cut plastic coating showed great rusting only on the unprotected metal edge, but there was no zone of corrosion advancing from the edge between the metal and the plastic coating.

EXAMPLE 18

Restoration of metal with 3-glycidyloxypropanephosphonic acid diethyl ester

Four heavily rusted, disintegrating plates of common structural steel (thickness 2 mm) having a structure partially destroyed by rust were immersed for 5 minutes into a mixture consisting of 3-glycidyloxypropanephosphonic acid diethyl ester and 2% 3-aminopropanephosphonic acid diethylate (water content 18%). Complete wetting immediately took place and the slightly viscous liquid filled up all of the pores and all of the flaking produced by rust. Then the hardening was performed for 3 hours at 120° C. The dripping and hardening procedures were performed four times in all. Then the large cracks and holes in the sheets were filled by casting with the same solution on a Teflon polytetrafluoroethylene support. After hardening at 120° C, the resultant products were strong, fracture-resistant plates of steel with a plastic coating. No voids or unwetted areas were found in cross sections cut for examination.

EXAMPLE 19 (Test for Purposes of Comparison)

The tests were repeated similarly to Example 18 with a commercial epoxy resin instead of the substance of the invention, resulting in steel plates of lesser stability. Fractures showed voids and relatively large unwetted areas.

What is claimed is:

1. A method of protecting the surface of a metal which consists essentially of applying to said metal surface an organophosphorus compound of the formula

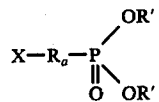

wherein
$a = 0$ or $1$
R is a branched or unbranched chain bivalent alkylene radical of 1 to 12 carbon atoms which is substituted or unsubstituted and can contain in the chain structures

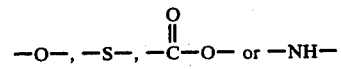

R' is a branched or unbranched chain alkyl radical of 1 to 12 carbon atoms which can be halogen substituted and which can contain in the chain structure

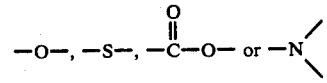

X is an epoxy ring, halogen, alkenyl, carboxylic acid ester residue, amino, isocyanato, isothiocyanato, urea, thiourea, urethano, alkyl substituted thio radical or the radical of a heterocyclic ring containing O, S or N in the ring structure.

2. A method according to claim 1 wherein X is chlorine.

3. A method according to claim 1 wherein X is bromine.

4. A method according to claim 1 wherein X is alkenyl of 2 to 8 carbon atoms.

5. A method according to claim 1 wherein X is a carboxylic acid ester residue, the ester function of which is an alkyl group of 1 to 8 carbon atoms, said residue having a saturated or unsaturated chain of between 2 and 8 carbon atoms attached to the carbonyl carbon atom.

6. A method according to claim 1 wherein X is an alkyl substituted thio radical wherein the alkyl group has between 1 and 8 carbon atoms.

7. A method according to claim 1 wherein X is a heterocyclic ring having between 3 and 7 members in the ring.

8. A method according to claim 1 wherein after said compound is applied to the metallic surface it is heated at a temperature of room temperature to 300° C.

9. A method according to claim 8 wherein said compound is heated at a temperature above 100° C.

10. A method according to claim 8 wherein said compound is applied to said surface while dissolved in a solvent.

11. A method according to claim 10 wherein said solvent is ethanol.

12. A method according to claim 8 wherein said compound is applied to said surface while maintained in a paint, lacquer, varnish, resin, plastic or rubber.

13. A method according to claim 12 wherein said compound is applied to said surface while maintained in an epoxy resin, polyester resin, phenolic resin, urea resin, vulcanizable polybutadiene resin, a natural olefinically unsaturated polymer, a synthetic unsaturated polymer or a drying oil derived from an unsaturated fatty acid.

14. A method according to claim 8 wherein between 0.05 and 200 grams of said compound are applied per square meter of surface area.

15. A method according to claim 1 wherein R' is a branched or unbranched chain alkyl radical of 1 to 5 carbon atoms.

16. A method according to claim 1 wherein said compound is applied to said surface and thereafter there is applied thereto a paint, lacquer, varnish, resin, plastic or rubber.

17. A method according to claim 1 wherein said compound is at least partially saponified.

18. A metal protected by a coating of an organophosphorus compound of the formula

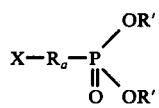

wherein
$a = 0$ or 1

R is a branched or unbranched chain bivalent alkylene radical of 1 to 12 carbon atoms which is substituted or unsubstituted and can contain in the chain structures

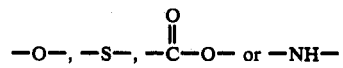

R' is a branched or unbranched chain alkyl radical of 1 to 12 carbon atoms which can be halogen substituted and which can contain in the chain structure

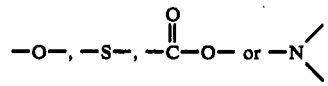

X is an epoxy ring, halogen, alkenyl, carboxylic acid ester residue, amino, isocyanato, isothiocyanato, urea, thiourea, urethano, alkyl substituted thio radical or the radical of a heterocyclic ring containing O, S or N in the ring structure.

19. A coated surface according to claim 18 wherein X is chlorine.

20. A coated surface according to claim 18 wherein X is bromine.

21. A coated surface according to claim 18 wherein X is alkenyl of 2 to 8 carbon atoms.

22. A coated surface according to claim 18 wherein X is a carboxylic acid ester residue, the ester function of which is an alkyl group of 1 to 8 carbon atoms, said residue having a saturated or unsaturated chain of between 2 and 8 carbon atoms attached to the carbonyl carbon atoms.

23. A coated article according to claim 18 wherein X is an alkyl substituted thio radical wherein the alkyl group has between 1 and 8 carbon atoms.

24. A coated article according to claim 23 having thereon a paint, lacquer, varnish, resin, plastic or rubber.

25. A coated article according to claim 18 wherein X is a heterocyclic ring having between 3 and 7 members in the ring.

26. A coated surface according to claim 18 wherein, upon the organophosphonic acid ester there is present a protective coating of an organic substance.

* * * * *

UNITED STATES PATENT AND TRADEMARK OFFICE
CERTIFICATE OF CORRECTION

PATENT NO. : 4,048,374
DATED : September 13, 1977
INVENTOR(S) : Hans-Joachim Kötzsch et al It is certified that error appears in the above-identified patent and that said Letters Patent are hereby corrected as shown below:

Title Page, Inventors, "Vahlensick" should read -- Vahlensieck --.

Column 1, line 31, "found" should read -- known --.

Column 2, line 27, "a" should read -- as --.

Column 2, line 46, "diacetote" should read -- diacetate --.

Column 3, line 43, "protective" should read -- protection --.

Column 4, line 17, "helerocyclic" should read -- heterocyclic --.

Column 7, line 62, "(2)" should read -- (2b) --.

Column 12, line 6, "Methylphosphite" should read -- diethylphosphite --.

Column 16, line 43, delete "*" second occurrence.

Signed and Sealed this

Eleventh Day of April 1978

[SEAL]

Attest:

RUTH C. MASON
Attesting Officer

LUTRELLE F. PARKER
Acting Commissioner of Patents and Trademarks